(12) United States Patent
Geilen et al.

(10) Patent No.: US 9,963,644 B2
(45) Date of Patent: May 8, 2018

(54) CLEANING OF LIQUID HYDROCARBON STREAMS BY MEANS OF COPPER-CONTAINING SORBENTS

(71) Applicant: Evonik Degussa GmbH, Essen (DE)

(72) Inventors: Frank Geilen, Haltern am See (DE); Stephan Peitz, Oer-Erkenschwick (DE); Guido Stochniol, Haltern am See (DE); Markus Winterberg, Waltrop (DE); Dietrich Maschmeyer, Recklinghausen (DE); Armin Rix, Marl (DE); Mathias Vogt, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days. days.

(21) Appl. No.: 15/103,805

(22) PCT Filed: Nov. 5, 2014

(86) PCT No.: PCT/EP2014/073763
§ 371 (c)(1),
(2) Date: Jun. 10, 2016

(87) PCT Pub. No.: WO2015/086228
PCT Pub. Date: Jun. 18, 2015

(65) Prior Publication Data
US 2016/0326442 A1 Nov. 10, 2016

(30) Foreign Application Priority Data

Dec. 12, 2013 (DE) ........................ 10 2013 225 724

(51) Int. Cl.
C10G 25/00 (2006.01)
C07C 7/12 (2006.01)
(Continued)

(52) U.S. Cl.
CPC ............ *C10G 25/003* (2013.01); *B01J 20/06* (2013.01); *B01J 20/08* (2013.01); *B01J 20/2803* (2013.01);
(Continued)

(58) Field of Classification Search
CPC .......... C07C 11/08; C07C 7/12; C10G 25/003
See application file for complete search history.

(56) References Cited

U.S. PATENT DOCUMENTS

| 4,279,781 A | 7/1981 | Dienes et al. |
| 4,535,071 A | 8/1985 | Schneider et al. |

(Continued)

FOREIGN PATENT DOCUMENTS

| DE | 3914817 | 11/1990 |
| DE | 10160486 | 6/2003 |

(Continued)

OTHER PUBLICATIONS

US Oil and Refining Co. MSDS Naphtha Jul. 20, 2009, pp. 1-14.*
(Continued)

*Primary Examiner* — In Suk C Bullock
*Assistant Examiner* — Alyssa L Cepluch
(74) *Attorney, Agent, or Firm* — Michael Best & Friedrich LLP

(57) ABSTRACT

The invention relates to a method for cleaning hydrocarbon mixtures, in which a contaminated hydrocarbon mixture comprising hydrocarbons having three to eight carbon atoms is at least partly freed of impurities by contacting with a solid sorbent, wherein the hydrocarbon mixture is exclusively in the liquid state during contact with the sorbent. The object of the invention is to specify a process for cleaning liquid $C_3$ to $C_8$ hydrocarbon mixtures, which is based on a readily available but non-carcinogenic sorbent and which achieves better purities compared to traditional molecular (Continued)

Figure 1:
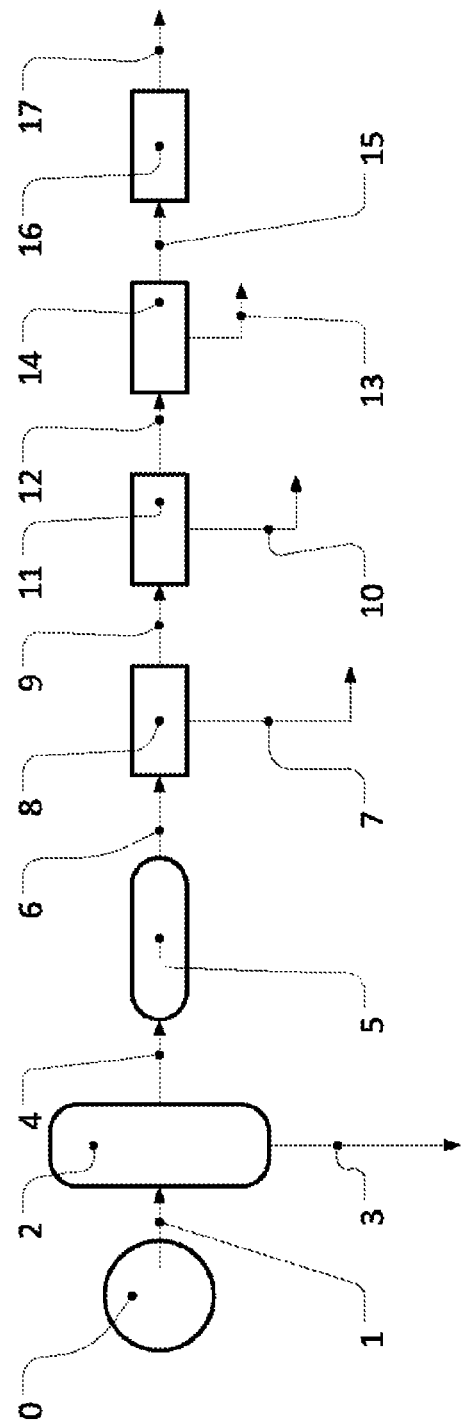

sieves. This object is achieved by using, as sorbents, solid materials of the following composition:
- copper oxide: 10% to 60% by weight (calculated as CuO);
- zinc oxide: 10% to 60% by weight (calculated as ZnO);
- aluminum oxide: 10% to 30% by weight (calculated as $Al_2O_3$);
- other substances: 0% to 5% by weight.

Materials of this kind are otherwise used as catalysts in methanol synthesis.

11 Claims, 2 Drawing Sheets

(51) Int. Cl.

| | |
|---|---|
| *C07C 7/13* | (2006.01) |
| *C10G 25/05* | (2006.01) |
| *C10G 53/08* | (2006.01) |
| *C10G 55/04* | (2006.01) |
| *C10G 57/00* | (2006.01) |
| *C10G 57/02* | (2006.01) |
| *C10G 67/06* | (2006.01) |
| *B01J 20/06* | (2006.01) |
| *B01J 20/08* | (2006.01) |
| *B01J 20/28* | (2006.01) |
| *C10G 53/14* | (2006.01) |
| *B01J 23/80* | (2006.01) |
| *B01J 35/00* | (2006.01) |

(52) U.S. Cl.
CPC ............... *C07C 7/13* (2013.01); *C10G 25/05* (2013.01); *C10G 53/08* (2013.01); *C10G 53/14* (2013.01); *C10G 55/04* (2013.01); *C10G 57/00* (2013.01); *C10G 57/005* (2013.01); *C10G 57/02* (2013.01); *C10G 67/06* (2013.01); *B01J 23/80* (2013.01); *B01J 35/0053* (2013.01); *B01J 2220/42* (2013.01); *C10G 2300/202* (2013.01)

(56) References Cited

U.S. PATENT DOCUMENTS

| | | | |
|---|---|---|---|
| 4,983,367 A | 1/1991 | Denny et al. | |
| 5,157,201 A | 10/1992 | Norris | |
| 7,749,376 B2* | 7/2010 | Turbevillle | B01J 20/06 |
| | | | 208/246 |
| 7,837,964 B2* | 11/2010 | Wessel | B01D 53/8603 |
| | | | 423/220 |
| 2007/0034552 A1 | 2/2007 | Turbeville et al. | |
| 2008/0306316 A1 | 12/2008 | Becker et al. | |
| 2015/0166475 A1 | 6/2015 | Peitz et al. | |

FOREIGN PATENT DOCUMENTS

| | | |
|---|---|---|
| DE | 102004018753 | 11/2005 |
| DE | 102008007081 | 8/2009 |
| DE | 102012212317 | 1/2014 |
| EP | 0125689 | 11/1984 |
| EP | 0320979 A2 | 6/1989 |
| EP | 1029839 | 8/2000 |
| WO | 94/28089 A1 | 12/1994 |
| WO | 02068119 | 9/2002 |
| WO | 2014009159 | 1/2014 |

OTHER PUBLICATIONS

Antos et al. Catalytic Naphtha Reforming, Revised and Expanded, Chapter 2. Feb. 23, 2004, pp. 107, 109, 111.*

International Search Report and Written Opinion, PCT/EP2014/073763, dated Jan. 21, 2015.

Tuberville, et al, "The Chemistry of Copper-Containing Sulfur Adsorbents in the Presence of Mercaptans," Catalysts Today, Elsevier, NL, vol. 116, No. 4, Sep. 15, 2006, pp. 519-525, XP027976148, ISSN: 0920-5861.

Intellectual Property Office of Singapore Search Report for Application No. 11201604637S dated Sep. 7, 2016 (3 pages).

* cited by examiner

CLEANING OF LIQUID HYDROCARBON STREAMS BY MEANS OF COPPER-CONTAINING SORBENTS

The invention relates to a process for purifying hydrocarbon mixtures, in which a contaminated hydrocarbon mixture comprising hydrocarbons having three to eight carbon atoms is at least partly freed of contaminants by contacting it with a solid sorbent, the hydrocarbon mixture being exclusively in the liquid state during the contact with the sorbent.

Hydrocarbons are compounds consisting exclusively of carbon and hydrogen. The nomenclature of the hydrocarbons is based on the number of carbon atoms present per molecule of the hydrocarbon. In abbreviated notation, the prefix $C_n$ is commonly used, where n is said number.

$C_4$ hydrocarbons are consequently compounds consisting exclusively of carbon and hydrogen, where the number of carbon atoms per molecule is four. Important representatives of the $C_4$ hydrocarbons are the alkenes and alkanes having four carbon atoms.

Mixtures of $C_4$ hydrocarbons are raw materials from downstream petrochemistry. They originate, for example, from steamcrackers (so-called "crack C4"), from catalytic crackers (so-called "FCC C4" (FCC: "fluid catalytic cracking") or "DCC C4" (DCC: "deep catalytic cracking"), from pyrolysis ("pyrolysis C4"), from MTO or MTP processes (MTO: "methanol to olefins", MTP: methanol to propylene) or dehydrogenations of isobutane and n-butane. The most common are $C_4$ hydrocarbons from steamcrackers (crack C4) and from catalytic crackers (FCC C4). Mixtures of $C_4$ mixtures of different origin are also traded, called "$C_4$ cut". For the purpose of utilizing the individual components, the $C_4$ mixtures have to be divided into their constituents with maximum purity.

The workup of $C_4$ streams from steamcrackers or catalytic crackers is described in principle in K.-D. Wiese, F. Nierlich, DGMK-Tagungsbericht [German Society for Petroleum and Coal Science and Technology, Conference Report] 2004-3, ISBN 3-936418-23-3. A comprehensive overall process description can be found in DE102008007081A1.

The aspects of $C_4$ workup that are relevant to this invention are outlined briefly hereinafter.

Technical $C_4$ hydrocarbon mixtures from the above-described sources typically contain not only saturated and monounsaturated compounds but also polyunsaturated compounds. Before individual compounds can be isolated from these mixtures, it is frequently necessary to remove other compounds to the maximum possible degree. This can be effected by physical methods, for example distillation, extractive distillation or extraction, but also by a selective chemical conversion of the components to be removed. Particular attention has to be paid to the maximum possible removal of the contaminants such as oxygen-, nitrogen- and sulphur-containing components present in the $C_4$ hydrocarbon mixture, since these can have adverse effects on the individual process steps as catalyst poisons. While these impurities are typically present only in traces in crack C4, they may also be present in higher concentrations, for example, in FCC C4 streams.

$C_4$ hydrocarbon mixtures from steamcrackers or fluidized catalytic crackers typically have the main components listed in Table 0 (contaminants not shown).

TABLE 0

Typical compositions of crack C4 and FCC C4

| Component | Crack C4 [% by wt.] | FCC C4 [% by wt.] |
| --- | --- | --- |
| isobutane | 1-3 | 20-40 |
| n-butane | 6-11 | 5-15 |
| 1-butene | 14-20 | 10-20 |
| 2-butenes | 4-8 | 20-35 |
| isobutene | 20-28 | 10-20 |
| 1,3-butadiene | 40-45 | less than 1 |

The composition of the raw materials may vary significantly according to the origin of the material. The $C_4$ components listed are supplemented by hydrocarbons having fewer or more carbon atoms, and contaminants such as mercaptans, sulphides, disulphides, nitrogen- and oxygen-containing compounds in small amounts.

In one variant, the workup of FCC C4 can be effected in such a way that the concentration of isobutane is first lowered by means of a distillative step in a distillation to a value of less than 5% by weight, more preferably less than 3% by weight. At the same time, the low boilers present in the mixture (for example $C_3$ hydrocarbons, light oxygen-, nitrogen- and sulphur-containing compounds) are removed or minimized. In the subsequent step, in a column, all the high boilers (for example $C_5$ hydrocarbons, heavy oxygen-, nitrogen- and sulphur-containing compounds) are removed via the bottom. In the next step, isobutene is removed, for example by reacting it with methanol to give methyl tert-butyl ether (MTBE), and the latter is removed by distillation. If pure isobutene is to be obtained, the methyl tert-butyl ether is subsequently cleaved again to isobutene and methanol.

For further workup of the $C_4$ mixture, the polyunsaturated compounds still remaining have to be converted with the aid of a selective hydrogenation process to the corresponding monounsaturated and saturated compounds. Now 1-butene and remaining isobutane can be removed by distillation in sufficient purity, and the remaining 2-butenes and the n-butane can be subjected to further workup. Frequently, the 2-butenes are converted by oligomerization, more specifically by dimerization to octenes. This forms one molecule having eight carbon atoms from two molecules each having four carbon atoms. The octenes can subsequently be converted by means of hydroformylation to PVC plasticizer alcohols. The saturated C4 hydrocarbons that remain after the olefins have been depleted can especially be used as propellants for aerosols.

An oligomerization is understood to mean a process in which higher alkenes having 6-20 carbon atoms are formed from olefins, such as, more particularly, from propene and butenes. An example of a process employed industrially is the nickel-catalysed OCTOL® process, which is described in detail in Hydrocarbon Process., Int. Ed. (1986) 65 (2. Sect. 1), pages 31 to 33, and in DE3914817, EP1029839 and DE102004018753.

The input streams used for the individual process steps have generally already attained a high degree of purity through preceding processes in which impurities were removed again and again. However, remaining impurities can reversibly or even irreversibly deactivate the catalyst. This deactivation should of course be reduced to a minimum for economic reasons. Therefore, as many catalyst poisons as possible should be kept away from the catalyst by further purification stages.

The various catalyst poisons present in the technical C₄ mixtures have poisoning effects in different ways. For instance, the acidic catalyst systems or system components such as cocatalysts are poisoned almost exclusively by components which are themselves basic or at least release bases as a result of further reactions. A particularly typical example of such substances is acetonitrile which, as a very weak base, is comparatively difficult to remove by sorption processes. However, it reversibly poisons strong Lewis acids. In the presence of traces of water, it is hydrolysed via acetamide to the strong base ammonia, which then irreversibly deactivates Brønsted acids as well through formation of ammonium ions. Incidentally, even water itself is always a partial catalyst poison, but the effect thereof is generally reversible, provided that it does not contribute to the formation of stronger catalyst poisons through further reactions. For the nickel-catalysed oligomerization of butenes over the OCTOL® catalyst, even a water content of about 5 ppm leads to measurable deactivation. However, the water is added onto olefins by many systems, and the alcohols formed are oxidized by the standard catalyst systems via a transfer hydrogenation, with hydrogenation of other unsaturated components, until thermodynamic equilibrium has been attained.

The metal complex catalysts too are sensitive to basic substances. The poisoning effect is usually manifested primarily via the deactivation of the acidic cocatalyst.

The metal component of the catalysts, in contrast, is attacked particularly strongly by components such as sulphur in the form of particular compounds, and this under particular circumstances irreversibly destroys the metal hydride or metal complex through formation of sparingly soluble sulphides. Since the metals are generally in very low oxidation states, sulphur compounds that are able to oxidize the metals to a relatively high oxidation state, for example di- and polysulphides, are particularly effective. Different sulphur compounds are thus able to have quite different primary effects. While, for example, disulphides react extremely efficiently to give thioethers and sulphur, which then oxidizes the metal hydrides to form sulphides, the primary effect of thioethers themselves at first is probably solely as a Lewis base. Through further processes and reactions, which are generally not even known in detail, with further trace components in the system, however, they also lead ultimately—albeit much more slowly—to the formation of metal sulphides as well.

According to the above statements, for maximum economic viability of operation of a plant for fractionation of hydrocarbon mixtures into their constituents of value with the aid of catalytic reaction units, the problem is thus to protect catalysts with maximum efficacy from catalyst poisons and especially sulphur compounds. The more reactant the catalyst is to specifically convert, the more strongly this applies, and so this applies particularly to heterogeneous catalysts such as those of the OCTOL® process.

Sulphur-containing poisons are generally removed by an alkaline scrub in the propene and butene streams in question. In this scrub, hydrogen sulphide and mercaptans react particularly efficiently. In general, the alkaline scrubbing solutions are regenerated by oxidation with air.

Such a scrubbing process is offered for industrial use by UOP LLC under the MEROX® name (G. A. Dziabis, "UOP MEROX PROCESS" in Robert Meyers, Handbook of Petroleum Refining Processes, 3rd Edition, 2004 McGraw-Hill).

In the MEROX® process, the mercaptans are oxidized in the aqueous scrubbing solution to di- and polysulphides, which are removed as oily phase. However, a small portion of these di- and polysulphides remains dissolved or suspended in the aqueous alkali metal hydroxide solution, and it is often not possible even by scrubbing this aqueous phase with a scrubbing oil or the like to quantitatively remove this residue before recycling into the scrubbing, such that the mercaptans are substantially removed but, on the other hand, small amounts of di- and polysulphides are introduced back into the stream. As just mentioned, these are sulphur components which convert the metal hydrides that are essential to the reaction to sparingly soluble metal sulphides and hence irreversibly deactivate the catalyst. Typically, for example, the streams of FCC C4 contain about 100 to 200 ppm of sulphur. After the MEROX® scrub, this content has then typically been reduced to a value below 10 ppm, and the sulphur compounds then consist predominantly of the di- and polysulphides mentioned, but also of higher mercaptans.

In practice, a portion of the poisons, through skilful arrangement of separating operations, for example distillations, can also be directed into fractions in which they no longer come into contact with sensitive catalysts. Frequently, however, this is not possible to the extent that seems desirable with regard to the purity of the streams, such that sorbents have to be inserted upstream of the catalyst beds, in order to assure the required purity.

Sorbents are solid substances that are capable of binding another substance, called the sorbate, if they come into contact with the sorbate. The binding is effected at the surface of the sorbent through physical and/or chemical effects. In this respect, a distinction is made between physical and chemical adsorption. Since the mode of action of a sorbent is not always unambiguously clear, reference is made here to a sorbent, without attributing the effect.

From a technical point of view, sorbents should generally be distinguished into those which are regeneratable and those that irreversibly convert or chemically bind the catalyst poisons.

Regeneratable sorbents used are frequently molecular sieves and zeolites. Regeneratable sorbents bind soiling materials only with moderate strength. In the course of regeneration of the sorbent, conditions such as higher temperatures and lower pressures, for example, under which the sorbent releases the sorbate again, are established. These properties lead to a relatively low capacity before breakthrough. In addition, high operating costs often arise through discharge and flushing of the sorbent and through the provision and disposal of the regenerating gases or else of the liquid streams.

Irreversible sorbents, in contrast, are not regenerated but disposed of after breakthrough. They therefore have to be available and disposable inexpensively. Since irreversible sorbents chemically bind the adsorbate, the permeability thereof with respect to the substances to be absorbed is lower than in the case of regeneratable sorbents. Irreversible sorbents therefore achieve better purity levels than regeneratable sorbents.

EP 0 064 464 A1 describes catalyst materials usable particularly for desulphurization of hydrocarbon batches. The catalyst materials contain copper oxide and are based on a support composed of alumina or type X or Y zeolite. A matter of concern is the obligatory content of cadmium oxide, since cadmium is classified as carcinogenic. Carcinogenic substances can be handled and disposed of only with high cost and inconvenience, and so particularly the irreversible use of such catalyst materials is uneconomic.

EP 0 354 316 B1 describes the cadmium-free fine desulphurization of liquid C₄ hydrocarbon mixtures over zeolites containing copper, silver and zinc. The preferred temperature range is between 50 and 130° C., the preferred pressure 1 to 50 bar. The weight hourly space velocity is reported as 1 to 40 h$^{-1}$. Even though the sorbent described here does not contain any potentially hazardous cadmium, this material is likewise uneconomic because of its high silver content of at least 2% by weight.

Nickel-containing oligomerization catalysts are particularly prone to catalyst poisons. Hydrocarbon mixtures having two to four carbon atoms often serve as substrate for oligomerizations such as the OCTOL® process. In order to effectively remove catalyst poisons, it has been found to be useful to pass such streams over a molecular sieve before entry into the oligomerization. For instance, EP0395857B1 describes a process of this type, in which a desulphurization of refinery propene, prior to oligomerization thereof, is effected over a copper-exchanged X zeolite at a temperature of 120° C., a pressure of 50 bar abs. and a weight hourly space velocity of 0.75 h$^{-1}$. Under these conditions, propene is supercritical.

Since these simple molecular sieves are readily available and do not present any potential hazard to health, they are nowadays the sorbents of choice in industrial practice for fine desulphurization of $C_3$ to $C_8$ hydrocarbon mixtures. Since the molecular sieves bind the contaminants only by physical means, sorbents of this kind can be regenerated. However, the sorption capacity thereof is lower compared to chemical sorbents, such that only moderate purities are achievable by fine desulphurization over zeolites.

With respect to this prior art, the problem addressed by the invention is that of specifying a process for purifying liquid $C_3$ to $C_8$ hydrocarbon mixtures, which is based on a readily available but non-carcinogenic sorbent and which achieves better purity levels compared to conventional molecular sieves.

At the same time, the process should also have the following properties:
  the sorbent used should have a maximum binding capacity for sulphur compounds and remove them substantially completely from the contaminated hydrocarbon mixture;
  the process should incur low operating costs; more particularly, it should be operable without the permanent supply of additional operating materials, for example hydrogen;
  the sorbent should be usable "out of the box" without any pretreatment, such as a hydrogenation or oxidation;
  it should be possible to handle the sorbent without risk; more particularly, it should not exhibit any pyrophoric properties;
  there should be no loss of olefinic materials of value over the sorbent through side reactions such as oligomerization, isomerization or hydrogenation.

This problem is surprisingly solved by using, as the sorbent, solid materials of the following composition:
  copper oxide: 10% to 60% by weight (calculated as CuO);
  zinc oxide: 10% to 60% by weight (calculated as ZnO);
  aluminium oxide: 10% to 30% by weight (calculated as $Al_2O_3$);
  other substances: 0% to 5% by weight.

The invention therefore provides a process for purifying hydrocarbon mixtures, in which a contaminated hydrocarbon mixture exclusively in the liquid state, comprising hydrocarbons having three to eight carbon atoms, is at least partly freed of contaminants by contacting it with a solid sorbent of the following composition that adds up to 100% by weight:
  copper oxide: 10% to 60% by weight (calculated as CuO);
  zinc oxide: 10% to 60% by weight (calculated as ZnO);
  aluminium oxide: 10% to 30% by weight (calculated as $Al_2O_3$);
  other substances: 0% to 5% by weight.

The sorbents used in accordance with the invention are commercially available in a simple manner, namely as catalysts for methanol synthesis:

In the field of methanol synthesis, copper/zinc/aluminium catalysts have been found to be useful in industry. Methanol is synthesized from carbon monoxide and hydrogen, or as a side reaction from carbon dioxide and hydrogen, which additionally gives water. Both reactions are thus conducted in the presence of the reactant hydrogen. When copper/zinc/aluminium catalysts are used, the methanol synthesis is conducted at temperatures between 220° C. and 230° C. and a pressure of about 5 MPa (50 bar). Under these conditions, the reactants and products are in the gas phase.

Copper/zinc/aluminium catalysts for methanol synthesis have been described many times in the patent literature:

For instance, DE2846614C3 discloses a process for preparing methanol from a gas mixture of CO, $CO_2$ and $H_2$ at temperatures of 200 to 350° C. in the presence of a catalyst containing 38.3% Cu, 48.8% Zn and 12.9% Al.

DE1568864C3 points out that synthesis gas should be desulphurized for methanol production, since copper catalysts can easily be poisoned with sulphur. The copper/zinc/aluminium catalyst described here contains more than 35% by weight of copper; the zinc content is 15% to 50% by weight. The aluminium content is reported as 4% to 20% by weight.

EP0125689B2 describes a catalyst for methanol synthesis, which comprises copper oxide and zinc oxide as catalytically active substances, and also—as a thermally stabilizing substance—aluminium oxide. In the unreduced state, catalyst precursors produced by way of example have, for instance, 65% to 68% by weight of CuO, 21% to 23% by weight of ZnO and 10% to 12% by weight of $Al_2O_3$. The specific surface area is 100 to 130 g/m$^2$. The methanol synthesis is effected at 250° C. and 50 bar.

Similar methanol catalysts having 63% to 65% by weight of CuO, 24% to 27% by weight of ZnO and 10% to 11% by weight of $Al_2O_3$ are described in DE10160486A1.

A catalyst having a comparatively low copper content and high zinc content (43.2% by weight of CuO, 47.0% by weight of ZnO and 10.2% by weight of $Al_2O_3$) was produced in U.S. Pat. No. 4,279,781. However, the catalytic activity thereof in methanol synthesis was rated as comparatively poor.

Because of the great industrial significance of the synthesis of methanol, a commodity chemical, copper/zinc/aluminium catalysts have not just been described in theoretical terms in the patent literature but are also readily commercially available. The disposal thereof is comparatively unproblematic, since no carcinogenic substances are present. Incidentally, the recycling of such sorbents is economically attractive, since this material contains a large amount of valuable copper.

The invention is based partly on the finding that commercially available methanol catalysts are suitable for purification of typical raw material streams in downstream petrochemistry. This is because it has been found that catalysts of this kind, when they are contacted with liquid hydrocarbon mixtures as sorbents, react well with the sulphur compounds even without supply of hydrogen. They react particularly quickly with mercaptans.

The invention therefore also provides for the use of a solid having the following composition:
- copper oxide: 10% to 60% by weight (calculated as CuO);
- zinc oxide: 10% to 60% by weight (calculated as ZnO);
- aluminium oxide: 10% to 30% by weight (calculated as $Al_2O_3$);
- other substances: 0% to 5% by weight for purification of liquid hydrocarbon mixtures comprising hydrocarbons having three to eight carbon atoms.

The usability of methanol catalysts based on $CuO/ZnO/Al_2O_3$ that has been recognized in accordance with the invention for removal of poisons from hydrocarbon mixtures is surprising because the methanol synthesis is always effected in the presence of hydrogen, whereas hydrogen is generally not present to a significant degree in the streams from which poisons are to be removed. Thus, crack C4 and FCC C4 streams that are customary on the market are free of hydrogen (<1 ppm by weight). The removal of poisons from such streams is thus effectively effected in the absence of hydrogen.

Furthermore, the workup of $C_3$ to $C_8$ hydrocarbon mixtures is generally effected in the liquid phase, since the hydrocarbons having more than two carbon atoms are liquefied with a low level of expenditure and can then be processed with a high process intensity. However, methanol synthesis is effected exclusively in the gas phase. It was not to be expected that materials intended for gas phase catalysis would also be suitable for liquid phase sorption.

In principle, any commercially available Cu/Zn/Al catalyst is suitable as a sorbent for purification of the $C_3$ to $C_8$ hydrocarbon mixtures. However, preference is given to using those catalysts which have the following composition:
- copper oxide: 30% to 45% by weight (calculated as CuO);
- zinc oxide: 30% to 50% by weight (calculated as ZnO);
- aluminium oxide: 10% to 15% by weight (calculated as $Al_2O_3$);
- further metal oxides: 0% to 2% by weight;
- graphite: 0% to 3% by weight;
- other substances: 0% to 1% by weight.

Useful further metal oxides in this context are, for example, iron oxides or magnesium oxides. Heavy metal oxides, which are known to be hazardous to health, for example cadmium or lead or chromium, should not be present if possible. Small amounts of graphite or magnesium stearate serve as binders for better shaping of the sorbent. "Other substances" in this context are understood to mean production-related contaminants of the sorbent.

With regard to the shaping, the sorbent may be present in powder form or in the form of granules. In addition, the sorbent can be pressed into a macroscopic form, for example into spheres, or into pellets or into rings.

Suitable methods for the production of the sorbent are in principle all the technical methods that lead to a solid having sufficient stability for handling. It encompasses essentially the two steps of:
- y) providing a porous framework material composed of aluminium oxide and/or graphite;
- z) blending the framework material with copper oxide and zinc oxide.

It is possible to use copper oxide powder, copper carbonate powder or hydroxide-containing copper compounds, and mixtures thereof. In the case of copper, it is also possible to convert a copper carbonate-containing compound, with the aid of an ammoniacal solution, fully or partly to a copper tetraammine carbonate solution which serves as starting material. These substances are mixed, in accordance with the inventive mixing ratios, together with zinc oxide, zinc carbonate or zinc hydroxide and an $Al_2O_3$-containing powder. Instead of $Al_2O_3$, it is also possible to partly use $SiO_2$. As $Al_2O_3$-containing powder, it is possible to use all the polymorphs of $Al_2O_3$, and also aluminium oxide hydrate or aluminium hydroxy oxides and aluminium hydroxide. The individual solid components can be blended and homogenized in suitable mixers, intensive mixers or kneaders. In this process, it is customary to undertake moistening with demineralized water. Adequate mixing may be followed by any suitable shaping operation. Under some circumstances, complete or partial drying and/or grinding of the mixture is necessary beforehand. For the shaping, extruders or tableting presses, for example, are suitable. Pan pelletizers may be appropriate for these purposes. In the case of tableting, a lubrication aid such as graphite is often added to the mixture. In the case of extrusion, other organic additives suitable for establishing the necessary plasticizability of the mixture are often chosen. These include, for example, cellulose-like substances, polyethers, polyethylene glycol and others, which may under some circumstances also act as pore formers when the substances are removed wholly or partly by a thermal treatment which generally follows the shaping operation. In the case of pelletization in a corresponding pan pelletizer, the buildup agglomeration is achieved by the gradual addition of a suitable amount of water.

The thermal treatment is conducted in one step or in sequential steps. Water components or else organic components are removed here, and the mechanical strength of the shaped body is generally increased in the process. In addition, the necessary oxide phases are formed if the precursor materials were not yet in this form.

In another mode of preparation, nitrate salts are used in aqueous solution or the oxidic compounds are fully or partly dissolved with nitric acid. Especially in the case of the aluminium oxide-type compounds, complete dissolution is often not effected; instead, the material is modified with the aid of the acid, this operation being referred to as peptization. The peptide is then mixed with the other dissolved components as described above and processed to a shaped body. The effect of heat treatment is that the respective oxides can form from the nitrates if the temperature has been suitably chosen.

Another effect of the use of nitrate-containing salt solutions may be that a precipitation reaction has to be conducted in order to arrive at a solids mixture. The pH is adjusted with sodium hydroxide or sodium carbonate solutions. Examples thereof can be found in U.S. Pat. No. 4,535,071.

In addition, it is possible to convert nitrate salt solutions to an oxidic product mixture in solid form by means of spray drying. In general, there then follow a grinding operation and a shaping operation as described above. A final heat treatment, which can also be conducted directly after the spray drying or the grinding of the constituents, brings about the necessary residual nitrate breakdown and converts the components to the oxides and consolidates the shaped body.

The above-described special production of the sorbent can be dispensed with through use of a commercially available methanol catalyst. Suitable examples are MegaMax® 700 and 800 from Clariant (formerly Süd-Chemie) and Haldor Topsoe's Mk-101 and Mk-121. These catalysts are described in Nitrogen+Syngas 290, November-December 2007, page 36.

In contrast to the methanol synthesis, the purifying process according to the invention is conducted in the absence of hydrogen. 100% absence of hydrogen can of course not be ensured in industry. The "absence of hydrogen" should therefore be understood to mean a hydrogen content of less than 1 ppm by weight, based on the total mass of the contaminated hydrocarbon mixture.

The sorbent is preferably deposited as a purifying bed directly upstream of the catalyst to be protected. It may be present in the same vessel as the catalyst to be protected (i.e. within the reactor) or in a vessel separately arranged upstream thereof. The arrangement of the purifying bed within the reactor is possible because no heat of reaction need be removed from or supplied to the sorbent. According to the circumstances, residence times between 0.01 and 0.2 hour are typically envisaged in the purifying bed, but if required also higher. Since operation at elevated temperature accelerates the depletion and increases the sulphur capacity, it is advantageous to arrange it downstream of the preheaters that are usually present. Observing a particular temperature of the sorbent is crucial to its purifying capacity. Experiments show that the contact should therefore take place at temperatures between 10° C. and 150° C., preferably between 20° C. and 130° C. and most preferably between 30° C. and 120° C. The optimal contact temperature is about 80° C. Since commercial methanol catalysts are used at much higher temperatures, thermal stability exists within these ranges. If the catalyst to be protected is operated at a different temperature, the sorbent should be disposed in a separate vessel, i.e. outside the reactor.

What is important is that the contaminated hydrocarbon mixture is exclusively in the liquid state during contact with the sorbent. Within the specified temperature range, this is assured by a pressure between 0.5 and 3.5 MPa (5 to 35 bar). However, the pressure is ultimately unimportant, provided that the hydrocarbons are in the liquid state. The weight hourly space velocity (WHSV) is then preferably selected between 0.5 and 7 $h^{-1}$. This means that between 0.5 and 7 kilograms per hour of contaminated hydrocarbon mixture are run through the purifying bed per kilogram of sorbent. The purifying bed consists of a bed of the sorbent having a bulk density in the range from 0.7 to 1.5 $kg/m^3$, preferably about 1.15 $kg/m^3$.

The sorbent is typically supplied in an oxidized state, which permits handling at room temperature under air. After the reactors have been filled, there is no need to activate the sorbents by a post-reduction. Even after use, the sorbents need not be stabilized by oxidation with air, and so they can be removed from the reactor in a simple manner.

In order to achieve particularly effective purification and to avoid interruptions to operation resulting from exchange of the sorbent, it is advisable to use a plurality of vessels which can be connected in series in a revolving manner such that the vessel having the highest loading is always disposed at the inlet and that with the lowest loading at the outlet. In this case, without interrupting the stream to be purified, at least one vessel can be taken out and the material present therein can be rinsed and removed, followed by refilling in an analogous manner.

The use of material having a high copper oxide surface area is advantageous because the reaction rate of the adsorption and of the conversion correlates therewith, and these materials also have a higher sorption capacity. Preferably, the sorbent has a copper oxide surface area of at least 50 $m^2/g$, preferably 100 $m^2/g$, based on the copper oxide content thereof. This promotes the sorptive action. The surface area is determined by nitrogen sorption.

What is important in the context of the present invention is that the sorbent has essentially no catalytic activity in respect of hydrogenation, etherification, oligomerization or further reactions of olefins. These reactions of hydrocarbons are to proceed exclusively over the catalysts intended therefor, and not in the purifying bed. The catalysts to be protected are thus outside the purifying bed, at least in another bed or in other apparatuses.

The process according to the invention is suitable in principle for the purifying of all hydrocarbon mixtures, preferably of those having three to eight carbon atoms. Hydrocarbon mixtures of industrial relevance are regarded as being, for example, propene, n-butenes, n-pentenes, hexenes, neohexene, etc., and the saturated analogues thereof. Among these, propane/propene and the butanes/butenes are absolutely the most important.

The inventive sorbent can be used particularly advantageously for purification of typical $C_4$ hydrocarbon streams in a state of workup immediately prior to conversion of the butenes present therein. The "contaminants" include, as well as the sulphur-containing compounds, also bases such as amines or nitriles, for example, although these are below the detection limit.

The process is of particularly good applicability to such mixtures, since it efficiently removes contaminants that act as poisons to the heterogeneous aluminium-, silicon- or nickel-containing oligomerization catalysts.

The impurities that are to be removed in accordance with the invention from the contaminated hydrocarbon mixture are preferably organic sulphur compounds that act as catalyst poison in the subsequent workup of the hydrocarbon mixture. The organic sulphur compounds that are harmful to catalysts and are present in the raw material streams typically obtainable include especially:
 a) thiols having the general formula R—SH
 b) disulphides having the general formula R—S—S—R'
 c) sulphides having the general formula R—S—R' and
 d) substituted or unsubstituted sulphur-containing heterocycles, such as thiophenes and/or thiolanes in particular.

In the above-specified structural formulae, R and R' may be identical or different alkyl, aryl, cycloalkyl or alkenyl radicals, where R and R' are especially methyl, ethyl, propyl, butyl, phenyl, cyclohexyl or butenyl radicals.

The particular advantage of the sorption material used in accordance with the invention is that it chemically adsorbs the contaminants, especially by arresting thiols present as contaminant at the surface of the sorbent. Any disulphides are converted to a thiol over the sorbent and then arrested. Chemisorption results in a particularly high level of purification, such that the hydrocarbon mixture is freed virtually completely of thiols and disulphides.

The chemisorption of the catalyst poisons is irreversible. For this reason, the sorbent used in accordance with the invention cannot be regenerated. This means that highly contaminated hydrocarbon streams rapidly exhaust the sorbent, such that it has to be exchanged. In the interests of economically viable operation of the purifying process, the proportion by weight of the contaminants in the contaminated hydrocarbon mixture, based on the total weight thereof, should be less than 0.2% by weight. More preferably, the contaminated hydrocarbon mixture contains less than 100 ppm by weight and more preferably less than 10 ppm by weight of impurities, in each case calculated as sulphur. In the case of such a low level of contamination, the sorbent can be operated for a very long period and additionally enables virtually complete removal of the catalyst poisons.

The typical raw material mixtures originating from mineral oil refineries have sulphur contents well above 0.2% by weight. For this reason, it is necessary to prepurify the raw material mixture in a prepurification stage upstream of the sorptive purification. In the prepurification stage, the more highly contaminated raw material mixture is prepurified to obtain a hydrocarbon mixture having a contamination level below 0.2% by weight.

A suitable prepurification stage is especially the above-described MEROX® scrub or a thioetherification, as disclosed in DE102012212317A1, which was yet to be published at the priority date of the present application.

The inventive form of purification is especially suitable for being inserted into the flow as a safety net filter beyond a MEROX® scrub.

In this context, a safety net filter is understood to mean a second purifying instance which is arranged beyond a first purifying instance and which has the function of conclusively keeping residual amounts of the catalyst poisons that have not been captured by the first purifying instance away from downstream reaction steps or, in the case of disrupted operation in the first instance, of ruling out immediate damage to the downstream reaction steps.

Preferably, a MEROX® scrub serves as the first purifying instance, which separates out most of the catalyst poisons in relatively large amounts in advance. Only the mercaptans and disulphides that are not captured by the MEROX® scrub are then retained in the sorption bed in accordance with the invention. In the case of disrupted operation in the MEROX® plant, the sorbent takes on the full purifying function thereof and protects the oligomerization from immediate irreversible damage. Since the safety net filter in the normal state of operation takes on only a small amount of adsorbate, it can be designed such that it has a much smaller capacity than a MEROX® scrub. This corresponds to the speed at which it is exhausted in the event of a fault. The suitable dimensions of the safety net filter depend on how quickly the incoming mixture can be diverted.

Thioethers, being comparatively unreactive substances, are barely removed in MEROX® scrubs. In order to avoid excessively large concentrations on entry into the sorption bed, they are preferably removed in a distillation as high boilers at a suitable point in the process procedure upstream of the sorption bed.

In combination with a prepurification stage such as a MEROX® scrub, the sorbent described here can be used irreversibly without hesitation. An irreversible use in this context is understood to mean that no direct regeneration, i.e. recovery of the active sorbent, is effected as soon as it is deactivated. This does not rule out recycling of the spent sorbent by recovering the metals present therein, such as the copper in particular, by metallurgical means. This is because, in such a metallurgical treatment, the original composition of the sorbent is lost, and so it is not possible to speak of a regeneration in this context.

The process according to the invention is basically suitable for desulphurization of hydrocarbon streams having three to eight carbon atoms. However, it is used with particular preference for removing poisons from $C_4$ streams that are obtained as crack C4 or as FCC C4 or the corresponding raffinates thereof in the refining of mineral oil. Thus, the contaminated hydrocarbon mixture preferably fulfils one of the following specifications A, B, C and D, each of which adds up to 100% by weight, the stated proportions by weight each being based on the total weight of the contaminated hydrocarbon mixture:

Specification A:
  isobutane 20% to 40% by weight, preferably 30% to 37% by weight;
  n-butane 5% to 18% by weight, preferably 8% to 10% by weight;
  1-butene 5% to 15% by weight, preferably 12% to 14% by weight;
  isobutene 12% to 25% by weight, preferably 15% to 20% by weight;
  2-butenes 9% to 40% by weight, preferably 20% to 30% by weight;
  1,3-butadiene 0% to 3% by weight, preferably 0.5% to 0.8% by weight;
  water 0% to 1% by weight, preferably less than 0.1% by weight;
  contaminants, especially sulphur-containing hydrocarbons, less than 0.5% by weight, preferably less than 0.2% by weight;

Specification B:
  isobutane 0.6% to 8% by weight, preferably 1% to 7% by weight;
  n-butane 0.5% to 8% by weight, preferably 4% to 7% by weight;
  1-butene 9% to 25% by weight, preferably 10% to 20% by weight;
  isobutene 10% to 35% by weight, preferably 20% to 30% by weight;
  2-butenes 3% to 15% by weight, preferably 5% to 10% by weight;
  1,3-butadiene 25% to 70% by weight, preferably 40% to 50% by weight;
  water 0% to 1% by weight, preferably less than 0.5% by weight;
  contaminants, especially sulphur-containing hydrocarbons, less than 0.5% by weight, preferably less than 0.2% by weight;

Specification C:
  isobutane 0.6% to 8% by weight, preferably 1% to 7% by weight;
  n-butane 0.5% to 15% by weight, preferably 4% to 13% by weight;
  1-butene 9% to 40% by weight, preferably 10% to 35% by weight;
  isobutene 10% to 55% by weight, preferably 20% to 50% by weight;
  2-butenes 3% to 25% by weight, preferably 5% to 20% by weight;
  1,3-butadiene 0% to 1% by weight, preferably less than 0.8% by weight;
  water 0% to 1% by weight, preferably less than 0.5% by weight;
  contaminants, especially sulphur-containing hydrocarbons, less than 0.5% by weight, preferably less than 0.2% by weight;

Specification D:
  n-butane 10% to 30% by weight, preferably 25% to 30% by weight;
  1-butene 0.2% to 45% by weight, preferably 5% to 30% by weight;
  2-butenes 35% to 85% by weight, preferably 50% to 75% by weight;
  water 0% to 1% by weight, preferably less than 0.1% by weight;
  contaminants, especially sulphur-containing hydrocarbons, less than 0.5% by weight, preferably less than 0.1% by weight.

Specification A describes typical FCC C4, while specification B describes typical crack C4. Specification C describes a typical raffinate I from crack C4. Specification D describes a raffinate III from FCC or CC4.

After the contaminated hydrocarbon mixture has been freed of its catalyst poisons in accordance with the invention, the customary workup of such mixtures can be effected, without any risk of poisoning the catalysts used downstream. The typical workup steps that may follow the purification described here include:

a) extraction of 1,3-butadiene present in the hydrocarbon mixture;
b) selective hydrogenation of diolefins and/or acetylenes present in the hydrocarbon mixture to olefins;
c) oligomerization of olefins present in the hydrocarbon mixture to corresponding oligomers;
d) distillative removal of 1-butene and/or isobutane present in the hydrocarbon mixture, especially with the purpose of obtaining 1-butene and/or isobutane in high purity;
e) removal of isobutene present in the hydrocarbon mixture by conversion of the isobutene with water to tert-butanol and/or with methanol to methyl tert-butyl ether;
f) dehydrogenation of butanes present in the hydrocarbon mixture to butenes;
g) oxidative dehydrogenation of butenes present in the hydrocarbon mixture to butadiene;
h) alkylation of n-butene present in the hydrocarbon mixture with isobutane likewise present;
i) oxidation of hydrocarbons having four carbon atoms present in the hydrocarbon mixture for preparation of maleic anhydride.

It will be appreciated that not all the workup steps a) to i) enumerated need be conducted; it is also possible to conduct only individual workup steps. The sequence enumerated is not binding either.

Furthermore, individual workup steps among those enumerated may also be arranged upstream of the inventive purification, provided that they are not sensitive to the catalyst poisons. At least a nickel-catalysed oligomerization should be protected by the inventive sorbent, since organic sulphur compounds, even in very small concentrations, poison nickel catalysts.

If the hydrocarbon mixture used is also contaminated with water, it is advisable to free the water-contaminated hydrocarbon mixture of water before entry into the purifying bed, i.e. to dry it. The motivation for removing the water is as follows: Since homogeneously dissolved water in the mixture somewhat attenuates the action of the sorbent, the stream is preferably dried before entry into the purifying bed, for example by means of an azeotropic distillation (drying distillation).

Figure 2:
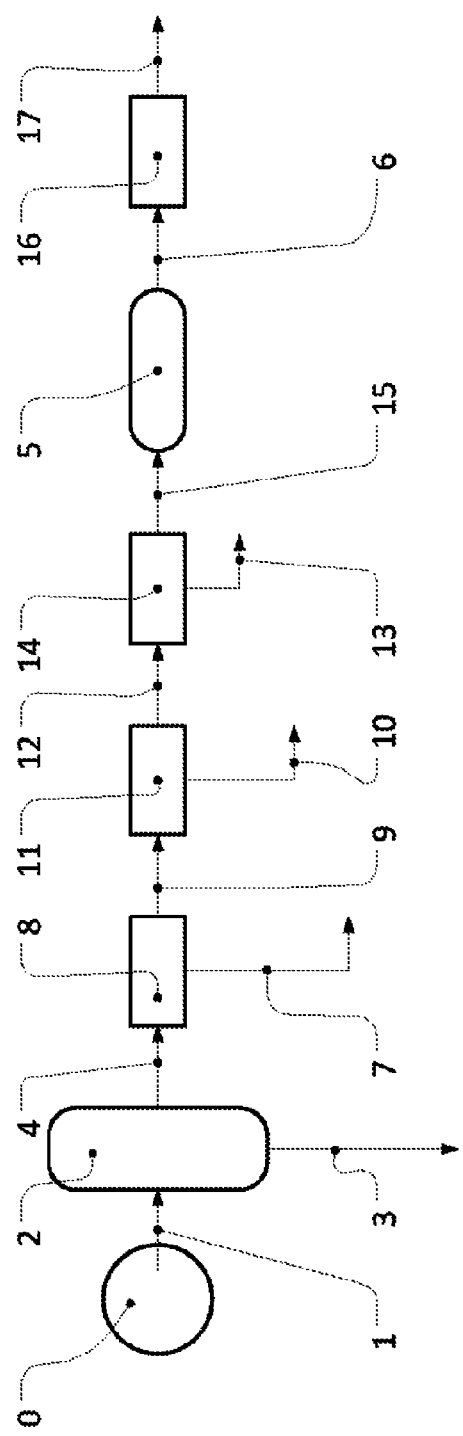

The basic structure of such value addition chains incorporating the inventive removal of poisons are to be illustrated in detail hereinafter. The figures show, in schematic form:

FIG. 1: $C_4$ line with coarse and fine desulphurization at the start;

FIG. 2: $C_4$ line with sorptive purification immediately upstream of the oligomerization.

FIG. 1 shows, in schematic form, a line for workup of $C_4$ hydrocarbon mixtures.

A raw material source 0 supplies a raw material mixture 1 comprising predominantly hydrocarbons having four carbon atoms (butenes and butanes). The raw material source 0 may, for example, be a mineral oil refinery. According to whether the cracker works by fluid catalysis or is operated as a steamcracker, a resulting raw material mixture 1 is referred to as FCC C4 or as crack C4.

Alternative raw material sources 0 or raw material mixtures 1 also include DCC C4 (DCC: "Deep catalytic cracking"), pyrolysis C4, C4 from MTO ("methanol-to-olefins") or MTP ("methanol-to-propylene") processes or $C_4$ from dehydrogenations of n-butane.

Since raw $C_4$ streams may have a high sulphur content depending on their source 0, the raw material mixture 1 is first coarsely prepurified in a prepurification stage 2, by removing sulphur-containing constituents 3 in relatively large amounts. The pre-purification stage 2 may, for example, be a MEROX® scrub or a thioetherification. Alternatively, it is also possible here to use a reversible sorbent which is regenerated cyclically. However, since the separation performance of a MEROX® scrub or a thioetherification is much greater, these prepurification stages are preferable over a sorptive coarse purification.

A hydrocarbon mixture 4 which is then drawn off from the prepurification stage 2 is still contaminated (contamination level max. 0.2% by weight, preferably below 100 ppm by weight). The contaminated hydrocarbon mixture 4, for complete elimination of the catalyst poisons present therein, is run into a purifying bed 5. The purifying bed 5 is a bed of a solid comprising copper oxide, zinc oxide and aluminium oxide, the sorbent. The purifying bed 5 is present in a vessel known per se. The liquid, contaminated hydrocarbon mixture 4 flows through the vessel, such that the sorbent present therein chemically adsorbs the contaminants present in the hydrocarbon mixture 4 and hence arrests them in the purifying bed 5. In this way, a purified hydrocarbon mixture 6 is obtained, which has been virtually completely freed of catalyst poisons.

In accordance with its material of value composition, a workup known per se is then effected on the materials of value present in the raw material mixture 1. If the raw material mixture 1 is crack C4, it has a high content of butadiene 7, which is removed by extraction in a butadiene removal 8.

Residues of unextracted butadiene are selectively hydrogenated (not shown). This gives what is called "raffinate I" 9.

The isobutene 10 present in the raffinate I is removed in an isobutene removal 11. The isobutene removal 10 generally involves an MTBE synthesis in which the isobutene is reacted with methanol to give methyl tert-butyl ether (MTBE) and a downstream MTBE cleavage in which the MTBE is cleaved back to isobutene 10.

The mixture which has been freed of isobutene is referred to as "raffinate II" 12. The material of value present therein, 1-butene 13, is distilled off in a 1-butene removal 14. This gives what is called "raffinate III" 15.

Raffinate III 15 contains, as material of value, essentially only the two 2-butenes, which are converted in an oligomerization 16 to $C_8$ olefins. The oligomerizate 17 is separated by distillation and subsequently processed by hydroformylation and hydrogenation to give plasticizer alcohols (not shown).

FIG. 2 shows one variant of a $C_4$ line in which the purifying bed 5 is arranged immediately upstream of the oligomerization 17. This is an option especially when a thioetherification which works in the presence of hydrogen is used as prepurification stage 2. Some of the hydrogen is also required beyond the butadiene removal 8, in order to selectively hydrogenate butadiene that has not been removed. Since the hydrogen is discharged from the $C_4$ line at a stage no later than the isobutene removal 11 or the 1-butene removal 14, the fine desulphurication then takes place in the purifying bed 5 in the absence of hydrogen.

Alternatively, the purifying bed 5 could also be charged with raffinate I 9. In that case, it would be arranged beyond the butadiene removal 8 and upstream of the isobutene removal 11 (not shown). This is advantageous especially when the raw material mixture 1 used is crack C4 containing large amounts of 1,3-butadiene according to specification B. 1,3-Butadiene could deactivate the sorbent too quickly. The purifying bed should therefore if at all possible be charged with a butadiene-depleted hydrocarbon mixture, i.e. at least with raffinate I or with FCC C4.

EXAMPLES

First Experiment: Removal of Ethanethiol According to the Invention

The sorbent used is a solid purchased from Clariant AG, which is usable as methanol catalyst. The sorbent contains about 42% by weight of CuO, about 44% by weight of ZnO, about 12% by weight of $Al_2O_3$ and about 2% by weight of graphite, and is in the form of tablets (5×3 mm). The specific copper oxide surface area, measured by means of nitrogen sorption, is 100 $m^2$ per g of copper oxide content.

120 g of sorbent are introduced into each of two reaction tubes having diameter 1 cm. The bulk density is about 1.2 kg/$dm^3$. The filled tubes are connected in series, with one sampling valve mounted between the tubes (discharge 1) and one at the end (discharge 2). The purifying beds are brought to a temperature of 80° C. by heating the tube walls, and a liquid mixture containing about 33% by weight of 1-butene, about 23% by weight of trans-2-butene, about 15% by weight of cis-2-butene and about 27% by weight of n-butane is allowed to flow through them at a pressure of 24 bar. As a contaminant, the material contains an average of 5.4 mg/kg of sulphur, predominantly in the form of ethanethiol. The loading of the purifying beds is 600 g/h, and so the sulphur input is about 3.2 mg/h.

As shown by the analyses, the sulphur is at first already removed virtually quantitatively from the mixture in the first purifying bed. From an operating time of 480 hours onward, the sulphur content at discharge 1 rises rapidly. This sharp breakthrough corresponds to an arrested amount of sulphur of about 1.7 g or a sulphur absorption in the purifying bed of about 1.4% by weight. The breakthrough downstream of the second purifying bed (discharge 2) takes place at about 1200 hours. At this time, the purifying beds have absorbed a total of about 3.9 g of sulphur, corresponding to a mean absorption of 1.7% by weight, based on the freshly introduced sorbent.

The discharge values of the individual $C_4$ components remained unchanged compared to the corresponding feed values over the entire experimental period.

After the end of this experiment, the beds are purged with nitrogen. The sorbent can be removed intact and with sufficient stability.

The results of the experiment are recorded in Table 1.

TABLE 1

Results from experiment 1

| Mean S content [% by wt.] in feed | Mean S content [% by wt.] in discharge 1 up to 480 h | Mean S content [% by wt.] in discharge 2 up to 1200 h | Mean decrease in S [% by wt.] in discharge 2 compared to feed up to 1200 h |
|---|---|---|---|
| 0.00054 | 0.00003 | 0.00002 | 96 |

Second Experiment: Removal of Methanethiol According to the Invention

The sorbent used and the experimental setup correspond to the first experiment.

Analogously to experiment 1, 5 mg/kg of sulphur are supplied as impurity, predominantly in the form of methanethiol. The loading of the two purifying beds, each of which has been charged with 28 g, is 380 g/h, i.e. the sulphur input is 1.9 mg/h. The contact temperature was set to 100° C.

As shown by the analyses, the sulphur is at first already removed virtually quantitatively from the mixture in the first purifying bed. From an operating time of about 410 hours onward, the sulphur content at discharge 1 rises. This sharp breakthrough corresponds to an arrested amount of sulphur of about 0.5 g or a sulphur absorption by the sorbent of about 1.9% by weight. The breakthrough downstream of the second purifying bed (discharge 2) takes place at about 720 hours. At this time, the purifying beds have absorbed a total of about 1.9 g of sulphur, corresponding to a mean absorption of 1.7% by weight, based on the freshly introduced sorbent.

The discharge values of the individual $C_4$ components remained unchanged compared to the corresponding feed values over the entire experimental period.

After the end of this experiment, the beds are purged with nitrogen. The sorbent can be removed intact and with sufficient stability.

The experimental results are shown in Table 2.

TABLE 2

Results from experiment 2

| Mean S content [% by wt.] in feed | Mean S content [% by wt.] in discharge 1 up to 410 h | Mean S content [% by wt.] in discharge 2 up to 720 h | Mean decrease in S [% by wt.] in discharge 2 compared to feed up to 720 h |
|---|---|---|---|
| 0.00044 | 0.00004 | 0.00004 | 91 |

Third Experiment: Removal of Diethyl Disulphide According to the Invention

The sorbent used and the experimental setup correspond to the first and second experiments.

Analogously to experiment 1, 1 mg/kg of sulphur are supplied as impurity, predominantly in the form of diethyl disulphide. The loading of the purifying beds, each of which contains 28 g of the sorbent, is 360 g/h, and so the sulphur input is about 0.4 mg/h. The operating temperature is 100° C.

As shown by the analyses, the sulphur is at first already removed virtually quantitatively from the mixture in the first purifying bed. From an operating time of 600 hours onward, the sulphur content at discharge 1 rises rapidly. This sharp breakthrough corresponds to an arrested amount of sulphur of about 0.3 g or a sulphur absorption by the sorbent of about 1.2% by weight. The breakthrough downstream of the second purifying bed (discharge 2) takes place at about 1080 hours. At this time, the purifying beds have absorbed a total of about 0.6 g of sulphur, corresponding to a mean absorption of 1.2% by weight, based on the freshly introduced sorbent.

The discharge values of the individual $C_4$ components remained unchanged compared to the corresponding feed values over the entire experimental period.

After the end of this experiment, the beds are purged with nitrogen. The sorbent can be removed intact and with sufficient stability.

The experimental results are shown in Table 3.

TABLE 3

Results from experiment 3

| Mean S content [% by wt.] in feed | Mean S content [% by wt.] in discharge 1 up to 600 h | Mean S content [% by wt.] in discharge 2 up to 1080 h | Mean decrease in S [% by wt.] in discharge 2 compared to feed up to 1080 h |
|---|---|---|---|
| 0.00010 | 0.00001 | 0.00001 | 90 |

Fourth Experiment: Removal of Dimethyl Disulphide with the Aid of Zeolites (not Inventive)

A sorbent is produced according to EP0354316. It is based on a type X zeolite and contains only 10% by weight of Cu. The two tubes, each charged with 50 g of the material, are connected in series, with one sampling valve mounted between the purifying beds (discharge 1) and one at the end (discharge 2). The beds are brought to a temperature of 120° C. by heating the tube walls, and a liquid mixture containing about 33% by weight of 1-butene, about 23% by weight of trans-2-butene, about 15% by weight of cis-2-butene and about 27% by weight of n-butane is allowed to flow through them at a pressure of 30 bar. As a contaminant, the material contains an average of 2.0 mg/kg of sulphur, predominantly in the form of dimethyl disulphide. The loading of the purifying beds is 375 g/h, and so the sulphur input is about 0.75 mg/h.

As shown by the analyses, the sulphur is at first already removed virtually quantitatively from the mixture in the first reactor. From an operating time of 48 hours onward, however, the sulphur content at discharge 1 rises rapidly. This sharp breakthrough corresponds to an adsorbed amount of sulphur of only about 0.036 g or a sulphur absorption by the sorbent of about 0.036% by weight. The breakthrough downstream of the second purifying bed (discharge 2) takes place at about 96 hours. At this time, the purifying beds have absorbed a total of about 0.07 g of sulphur, corresponding to a mean absorption of 0.07% by weight, based on the freshly introduced sorbent.

With the noninventive material, distinct desulphurization can accordingly be achieved only for a very short time, and the material used is not in any relation to the purifying performance.

The results are shown in Table 4.

TABLE 4

Results from experiment 4

| Mean S content [% by wt.] in feed | Mean S content [% by wt.] in discharge 1 up to 48 h | Mean S content [% by wt.] in discharge 2 up to 96 h | Mean decrease in S [% by wt.] in discharge 2 compared to feed up to 96 h |
|---|---|---|---|
| 0.00020 | 0.000005 | 0.000005 | 97 |

CONCLUSION

The experiments demonstrate that the sorbent used in accordance with the invention has the following properties:

it binds the sulphur from sulphur compounds virtually completely;

it does not require any activation in the hydrogen stream, nor any other additional operating materials;

it does not require any periodic purifying and desorption streams, since it is an irreversible sorbent;

it can be accommodated in a simple vessel through which the mixture simply flows, preferably at slightly elevated temperature, as is typically often necessary in any case for the feeding of downstream reactors;

it causes virtually no side reactions of olefins, such as oligomerization, isomerization and hydrogenation, and hence also no losses;

it does not release any substances whatsoever in concentrations that have any influence at all on the downstream processing stages;

in view of the long lifetime at typical sulphur concentrations below 5 ppmw and a capacity of at least 1% by weight of sulphur, it is very inexpensive to operate, even though it cannot be regenerated directly, and can instead only be sent to a raw material utilization after the capacity has been exhausted;

it can be handled and disposed of without any problem, since it is neither classified as carcinogenic nor exhibits pyrophoric properties.

LIST OF REFERENCE NUMERALS

0 raw material source
1 raw material mixture
2 prepurification stage
3 sulphur-containing constituents
4 contaminated hydrocarbon mixture
5 purifying bed
6 purified hydrocarbon mixture
7 butadiene
8 butadiene removal
9 raffinate I
10 isobutene
11 isobutene removal (MTBE synthesis/MTBE cleavage)
12 raffinate II
13 1-butene
14 1-butene removal
15 raffinate III
16 oligomerization
17 oligomerizate

What is claimed is:

1. Process for purifying hydrocarbon mixtures, in which a contaminated hydrocarbon mixture comprising hydrocarbons having three to eight carbon atoms is at least partly freed of contaminants by contacting it with a solid sorbent in the absence of hydrogen, the hydrocarbon mixture being exclusively in the liquid state during the contact with the sorbent, wherein the sorbent has the following composition that adds up to 100% by weight:

copper oxide: 10% to 60% by weight (calculated as CuO);
zinc oxide: 10% to 60% by weight (calculated as ZnO);
aluminium oxide: 10% to 30% by weight (calculated as $Al_2O_3$);
other substances: 0% to 5% by weight;
wherein the sorbent is supplied in an oxidized state without being activated by a reduction reaction; and
wherein the contact is effected under the following conditions:
temperature between 30° C. and 120° C.;
pressure between 0.5 and 3.5 MPa; and
weight hourly space velocity between 0.5 $h^{-1}$ and 7 $h^{-1}$.

2. Process according to claim 1, wherein the sorbent has the following composition that adds up to 100% by weight:
copper oxide: 30% to 45% by weight (calculated as CuO);
zinc oxide: 30% to 50% by weight (calculated as ZnO);
aluminium oxide: 10% to 15% by weight (calculated as $Al_2O_3$);
further metal oxides: 0% to 2% by weight;
graphite: 0% to 3% by weight;
other substances: 0% to 1% by weight.

3. Process according to claim 1, wherein the contaminated hydrocarbon mixture contains at least one impurity from one of the following substance classes:
 a) thiols having the general formula R—SH where R may be an alkyl, aryl, cycloalkyl or alkenyl radical;
 b) disulphides having the general formula R—S—S—R' where R and R' may be identical or different alkyl, aryl, cycloalkyl or alkenyl radicals;
 c) sulphides having the general formula R—S—R' where R and R' may be identical or different alkyl, aryl, cycloalkyl or alkenyl radicals;
 d) substituted or unsubstituted sulphur-containing heterocycles.

4. Process according to claim 1, wherein the proportion by weight of the contaminants in the contaminated hydrocarbon mixture, based on the total weight thereof, is less than 0.2% by weight.

5. Process according to claim 1, wherein the sorbent is used irreversibly.

6. Process according to claim 1, wherein the contaminated hydrocarbon mixture fulfils one of the following specifications A, B, C and D, each of which adds up to 100% by weight, the stated proportions by weight each being based on the total weight of the contaminated hydrocarbon mixture:
Specification A:
 isobutane 20% to 40% by weight;
 n-butane 5% to 18% by weight;
 1-butene 5% to 15% by weight;
 isobutene 12% to 25% by weight;
 2-butenes 9% to 40% by weight;
 1,3-butadiene 0% to 3% by weight;
 water 0% to 1% by weight;
 contaminants less than 0.5% by weight;
Specification B:
 isobutane 0.6% to 8% by weight;
 n-butane 0.5% to 8% by weight;
 1-butene 9% to 25% by weight;
 isobutene 10% to 35% by weight;
 2-butenes 3% to 15% by weight;
 1,3-butadiene 25% to 70% by weight;
 water 0% to 1% by weight;
 contaminants less than 0.5% by weight;
Specification C:
 isobutane 0.6% to 8% by weight;
 n-butane 0.5% to 15% by weight;
 1-butene 9% to 40% by weight;
 isobutene 10% to 55% by weight;
 2-butenes 3% to 25% by weight;
 1,3-butadiene 0% to 1% by weight;
 water 0% to 1% by weight;
 contaminants less than 0.5% by weight;
Specification D:
 n-butane 10% to 30% by weight;
 1-butene 0.2% to 45% by weight;
 2-butenes 35% to 85% by weight;
 water 0% to 1% by weight;
 contaminants less than 0.5% by weight.

7. Process according to claim 1, further comprising one or more of the following steps:
 a) extracting 1,3-butadiene from the hydrocarbon mixture which has been at least partly freed of contaminants;
 b) selectively hydrogenating diolefins, acetylenes, or diolefins and acetylenes in the hydrocarbon mixture which has been at least partly freed of contaminants to form olefins;
 c) oligomerizing olefins present in the hydrocarbon mixture which has been at least partly freed of contaminants to form oligomers;
 d) distilling the hydrocarbon mixture which has been at least partly freed of contaminants to remove 1-butene, isobutene or both 1-butene and isobutene from the hydrocarbon mixture which has been at least partly freed of contaminants;
 e) removing isobutene from the hydrocarbon mixture which has been at least partly freed of contaminants by converting the isobutene to tert-butanol with water or by converting the isobutene to methyl tert-butyl ether with methanol;
 f) dehydrogenating butanes present in the hydrocarbon mixture which has been at least partly freed of contaminants to form butenes;
 g) oxidatively dehydrogenating butenes present in the hydrocarbon mixture which has been at least partly freed of contaminants to form butadiene;
 h) alkylating n-butene present in the hydrocarbon mixture which has been at least partly freed of contaminants with isobutane present in the hydrocarbon mixture which has been at least partly freed of contaminants;
 i) oxidizing hydrocarbons having four carbon atoms present in the hydrocarbon mixture in the hydrocarbon mixture which has been at least partly freed of contaminants.

8. Process according to claim 3, where R and R' are each independently selected from a methyl, an ethyl, a propyl, a butyl, a phenyl, a cyclohexyl or a butenyl radical.

9. Process according to claim 3, where the substituted or unsubstituted sulphur-containing heterocycles comprise thiophenes, thiolanes or both thiophenes and thiolanes.

10. Process according to claim 1, wherein the proportion by weight of the contaminants in the contaminated hydrocarbon mixture, based on the total weight thereof, is less than 100 ppm by weight.

11. Process according to claim 1, wherein the proportion by weight of the contaminants in the contaminated hydrocarbon mixture, based on the total weight thereof, is less than 10 ppm by weight.

* * * * *